United States Patent

Schwarz et al.

[11] Patent Number: 5,998,202
[45] Date of Patent: Dec. 7, 1999

[54] MULTIPLE CHAMBER DIFFUSION VESSEL

[75] Inventors: Ray P. Schwarz, Friendswood; William J. Anderson, Richmond; S. Dan Dimitrijevich, Bedford, all of Tex.

[73] Assignee: Synthecon, Inc., Houston, Tex.

[21] Appl. No.: 09/028,986

[22] Filed: Feb. 25, 1998

Related U.S. Application Data

[60] Provisional application No. 60/039,119, Feb. 26, 1997.

[51] Int. Cl.$^6$ ................................................. C12M 3/00
[52] U.S. Cl. ................................... 435/298.2; 435/297.1
[58] Field of Search ....................... 435/289.1, 297.1, 435/298.2

[56] References Cited

U.S. PATENT DOCUMENTS

| | | | |
|---|---|---|---|
| 5,026,650 | 6/1991 | Schwarz et al. | 435/286 |
| 5,153,131 | 10/1992 | Wolf et al. | 435/240.24 |
| 5,665,594 | 9/1997 | Schwarz et al. | 435/394 |
| 5,763,279 | 6/1998 | Schwarz et al. | 435/383 |

*Primary Examiner*—David A. Redding
*Attorney, Agent, or Firm*—John R. Casperson; Wendy K.B. Buskop

[57] ABSTRACT

A bioreactor system features a vessel capable of being temperature controlled comprised of two or more cylindrical chambers separated by a common porous membrane. The chambers are capable of being mounted for rotation about a common horizontal axis, essentially creating a micro gravity environment, for the purpose of creating an interface between the chambers while maintaining fluid culture medium in at least one of the chambers and enabling cells to grow in the wells or pores disposed between the chambers. The device is formed by a tubular vessel having an inner surface and an outer surface, a first open end, a second open end and a longitudinal axis.

2 Claims, 1 Drawing Sheet

MULTIPLE CHAMBER DIFFUSION VESSEL

This application claims the benefit of US Provisional Application No. 60/039, 119 filed Feb. 26, 1997.

BACKGROUND

There has been long needed a device wherein problem cells, such as cancer cells like melanoma cells, can be grown in one chamber, and tissue to be effected by the problem cells (the target cells), grown in another, so that the interaction between the problem cells and the target cells can be observed. Normal tissue growth at the air/liquid interface, such as for skin, can be accomplished using this device. Additionally, there has been need for a device which operates in micro gravity to grow tissues and cells, in order to effectively and cheaply observe the growth of those cells.

SUMMARY OF THE INVENTION

The invention comprises a bioreactor system featuring a vessel capable of being temperature controlled and comprised of two or more cylindrical chambers separated by a common porous membrane(s) capable of being mounted for rotation about a common horizontal axis. The system essentially creates a micro gravity environment for the purpose of creating an interface between the chambers while maintaining fluid culture medium in at least one of the chambers and enabling cells to grow in the wells or pores disposed between the chambers.

Figures 1, 2:
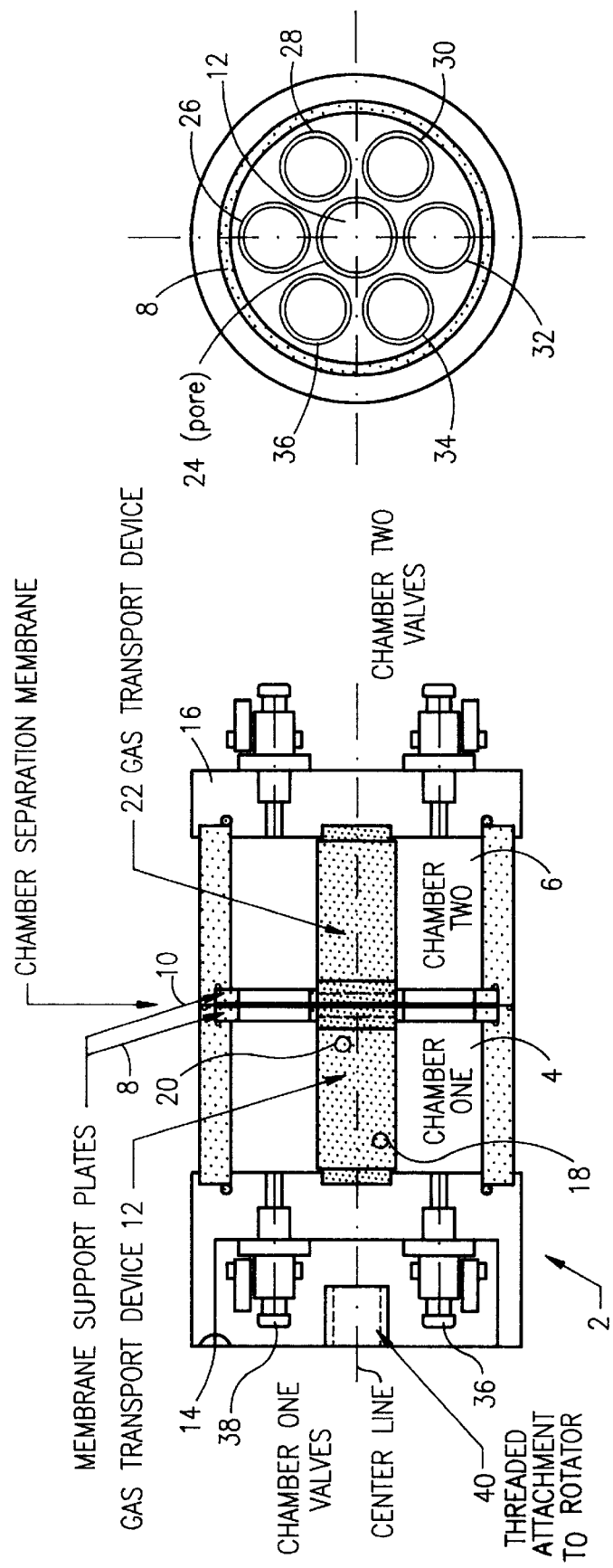
FIG. 1 is a side sectional view of a vessel in accordance with one embodiment of the invention.
FIG. 2 is a cross sectional view of the vessel shown in FIG. 1.

In one embodiment the device comprises the following features as show in FIG. 1. A cylindrical vessel (2) having two ends (14) and (16) and comprised of a clear plastic or crystalline polymer thereby enabling the researcher to see the growing cells in the culture medium inside the vessel.

The vessel (2) has at least two chambers (4) and (6) disposed between the ends (14) and (16). The two chambers (4) and (6) are connected via two membrane support plates (8) and (10) having approximately the same diameter as the chambers. Details of the typical membrane support plates (8) are shown in greater detail in FIG. 2. The membrane support plates, such as plate (8) shown in FIG. 2, comprise a center well or pore (24) for optionally allowing the gas transport device (12) to be integrally connected with gas transport device (22). The membrane support plates can comprise a plurality of wells or pores. In a preferred embodiment, the membrane support pates have six (6) wells or pores spaced equidistant from each other, with each well or pore having identical small inner diameters of 1 cm. The membrane support plates can have a wide variety of well or pore numbers, and the inner diameters of these wells or pores can range from a small I.D. of. 01 cm to over 1 cm I.D. The membrane support plates can be made of the same material as the walls of the chambers (4) and (6) which provide the researcher with the ability to see the materials in the chambers (4) and (6).

The chambers (2) and (4) are formed such that they can be detachably engaged with at least one membrane support plate and form a leak-tight and air tight environment inside the chambers. Additionally this formed integral connection provides the researcher with the ability to create a sterile environment inside the chamber without concern for harmful cells or materials to penetrate into the environment surrounding the vessel (2).

A gas transport device (12) is disposed in the vessel and may extend the length of the interior of one or more of the chambers of the cylindrical vessel. The gas transport device is for the bi directional transfer of dissolved gas into and out of each chamber and across the membrane. The gas transport device comprises at least one opening (18) which permits dissolved gas to flow from a source outside of the vessel (2) into the chamber (4) chamber (6) and to adjoining chambers. Additional openings (20) are provided in the gas transport device for the gas to exit. Gas transport device (12) is constructed in such a manner that it not only can be detachably engaged with ends (14) and (16), but additional gas transport members can be integrally connected together, thereby optionally enabling the researcher to connect a series of vessels (2) together.

In an optional embodiment, the gas transport device (12) can be connected in series to additional gas transport devices (22) such that gas transport device is detachably connected and capable of extending through both chambers (2) and (4) of the vessel. The gas transport device (12)can comprise a at least one carrier tube capable of being detachably engaged to the ends (14) and (16) of the vessel (2) such that a gas inflow tube (not shown) can be engaged to the end of the gas transport device (12).

Chambers (4) and (6) can be of the same size or of different sizes, however, if the chambers of are of different sizes, no direct connection between the chambers should exist, except for the gas transport device and except for the pores disposed in the membrane support plates (8) and (10).

Each end (14) or (16) of the vessel (2) comprises a plurality of through ports. In a preferred embodiment wherein the vessel has an overall length of 9.5 cm, each end, such as end (14) shown in FIG. 1 has 4 ports. Two of the ports (36) and (38) have a preferred inner diameter (ID) of 1 cm and are disposed near the perimeter of the end (1 4), and a third port (not shown) having an ID of 1.5 cm is located near the perimeter of the end (14). The fourth port (40) serves as the threaded attachment to a rotator (not shown) and also serves as a port wherein two of the gas transport devices can be integrally connected together. The ends of this preferred embodiment are preferably about 2 cm in thickness and an overall diameter of 7 cm.

Various methods for growing cells can be used with this vessel. In general, the following method is used to create a culture.

A vessel having two or more chambers is constructed. One membrane is disposed between the membrane support plates 8 and 10 between the chambers, providing a barrier between the chamber. Gas transport devices 12 and 22 are disposed in each chamber and both gas transport devices are detachably connected together. Each chamber is filled with a fluid culture medium and cells are added to each chamber containing the medium. The vessel is then closed. The vessel may be incubated for a period of hours or it may be directly connected to a rotating device, a typical rotating device is shown in U.S. Pat. No. 5,437,998 and is hereby incorporated by reference. The vessel 2 is then rotated about a generally horizontal axis to suspend cells or cell aggregate particles in the fluid culture medium. Upon growth of the cells and attachment to the membrane of the cellular material, the fluid in one chamber can be drained and replaced with air, a gas, or a gas mixture or alternatively, additional or different fluid mediums. Cells attached to the membrane can literally be exposed to a liquid environment in one chamber and a different fluid medium or gaseous environment on the other chamber.

The system involves rotating a fluid nutrient medium having zero headspace in one or more culture chambers. The porous membrane between the two chambers provides for transfer of nutrients and/or cell products between the chambers. This membrane between the chambers provide an attachment substrate for cells and tissues to grow upon.

In another embodiment, using gas in one chamber and liquid in the other the cells attach to the membrane so that the membrane becomes impermeable to liquids. The liquid in an (adjacent) chamber is removed to expose the other side to a gaseous phase.

This device makes it possible to simulate a normal environment by providing an air interface on one side and fluid on the other, much like the relationship epidermal cells have in the human body. For example, epidermal cells are exposed to air on one side (the side outside the body) and to a moist environment on the other side of the human body.

In the most preferred embodiment, the preferred method is as follows for using the vessel:

In a method for forming epidermal cells using a vessel to provide an air-liquid interface by exposing a surface of the tissue to air the steps comprise the following:

Step 1—clamping a nutrient permeable membrane to the center portion of the gas transport device of the vessel wherein the diameter of the membrane is essentially the same diameters as the chambers of the vessel;

Step 2—mixing cells into a collagen solution; wherein said membrane can comprise, man made polymers, such as polycarbonate or polypropylene or it can be a membrane made from collagen, such as those supplied by ICN pharmaceuticals. It is preferable that the membrane permits the passage of nutrients, such as amino acids, salts, serum components, or glucose through its pores. In the preferred embodiment, the membrane has a thickness of a maximum of 1 millimeter thickness. The preferred pore sizes of the membrane are between 2–6 microns, and can be of any shape. The pore structure of the membrane is preferably such that the pores pass through the entire thickness of the membrane.

Step 3—The six (6) wells or pores of the membrane support plates are filled with collagen solution containing fiber blasts. Preferably a collagen type 1 solution from ICN is used in a preferred quantity of 1–2 mils. It is preferred to use the collagen type 1 solution at an initial temperature of 4 degrees C.

Step 4—Cells to be studied are mixed into the collagen solution at a density 300,000 cells per 1 mil of solution. The device is then closed.

Step 5—The device is inserted into an incubator or approximately 2—3 hours without rotation until the collagen solution becomes a gel.

Step 6—The vessel is removed from the incubator and slowly the vessel is charged with growth medium so at not to disturb the collagen gel. The charging is performed under sterile conditions. The preferred growth medium is typically "DMEM" which is known as dulbeco's minimum essential medium to provide nutrients for the cells. Approximately 30 mils per side of growth medium at room temperature is disposed in a chamber.

Step 7—The vessel is placed into a rotating device, such as described in U.S. Pat. No. 5437998. The vessel is rotated for a longer period of time, such as about 48 hours, at approx. 30 revolutions per minute. The vessel possibly could be rotated faster to achieve the same results, or slower for longer periods of time and may obtain the same results.

Step 8—The vessel is removed from the rotating device.

Step 9—The growth medium is removed from the top side of the gels, using a pipette or syringe. The cells are still in the gel.

Step 10—Cells, such as epidermal cells, in a quantity of 200,000 cells per square centimeter are placed on the surface of the gel and the vessel is then moved to the incubator.

Step 11—The device with the cells is then incubated 4–5 hours at about 37° C. in sterile conditions.

Step 12—After incubation, each chamber is filled with 30–40 mils. of fresh medium KGM "keretinocytes growth medium" available from CLONETICS Corp. of San Diego, Calif.

Step 13—The vessel with the new medium in place is then rotated for approximately four (4) days, at a temperature of between 36.5° –37° C. (preferably 36.9° C.).

Step 14—The growth medium is then removed with a pipette.

Step 15—5 mils of fresh medium, preferably KGM medium is placed into each chamber of the vessel to make the surface of the culture moist.

Step 16—The vessel is then rotated for approximately 2 weeks, exposing the cells to air.

Step 17—At the end of 2 weeks, the vessel is then dismantled. In each pore of the membrane support plates, tissue of about the size of a U.S. nickel will have grown. Because of the membrane, with space on both sides, two types of cells can be grown. Each cell culture can be supported by its optimum media.

The inventors have created a most unique device using a reduced gravity or micro gravity environment and that allows this type of cell growth.

Any type of barrier tissue can be grown in this vessel using this methodology. Examples of typical tissue include cornea tissue, vaginal epithelia tissue, and blood vessel cells.

As a research tool, this vessel and the method can take portions of a tumor, such as melanoma, place the cells on the surface of the gel in one chamber, and target tissue, like liver can be placed in the other chamber. The growth of the cells and how the melanoma metatheses to the liver can then be studied at many stages. The inventors note that the same cells or tissues can be grown in each chamber with different culture materials or media in the other separate chambers. Alternatively, different cells or tissues can be grown in each chamber with the same or different cell culture materials or media.

What is claimed is:

1. An apparatus comprising:
    a tubular vessel having an inner surface and an outer surface, a first open end, a second open end and a longitudinal axis;
    a means for dividing the vessel into a first chamber and a second chamber, said means comprising
        a first plate and a second plate with a membrane positioned therebetween;
        wherein the first plate defines a plurality of openings;
        the second plate defines a plurality of openings; and
        the openings are aligned so that medium can move from one side to the other side;
    a first end cap removably attached to the first end, said first end cap having access ports;
    a second end cap removably attached to the second end, said second end cap having access ports;
    and a gas transport device.

2. Apparatus as in claim 1 further comprising a rotation means.

* * * * *

UNITED STATES PATENT AND TRADEMARK OFFICE
CERTIFICATE OF CORRECTION

PATENT NO : 5,998,202
DATED : December 7, 1999
INVENTOR(S) : Schwarz et al.

It is certified that error appears in the above-identified patent and that said Letters Patent are hereby corrected as shown below:

On the Title page, line 2: "Schwarz et al." is corrected to "Dimitrijevich et al."

block 75: "Ray P. Schwarz, Friendswwod; William J. Anderson, Richmond; S. Dan Dimitrijevich, Bedford, all of Tex."
is corrected to :
"S. Dan Dimitrijevich, Bedford; William J. Anderson, Richmond; Ray P. Schwarz, Friendswood, all of Tex."

Signed and Sealed this

First Day of May, 2001

*Attest:*

NICHOLAS P. GODICI

*Attesting Officer*     *Acting Director of the United States Patent and Trademark Office*